United States Patent [19]

Siker et al.

[11] Patent Number: 5,425,362
[45] Date of Patent: Jun. 20, 1995

[54] FETAL SENSOR DEVICE

[75] Inventors: Daniel Siker, Milwaukee; Michael T. Larsen, Wauwatosa; NC Joseph Lai, Brookfield, all of Wis.

[73] Assignee: Criticare, Waukesha, Wis.

[21] Appl. No.: 100,607

[22] Filed: Jul. 30, 1993

[51] Int. Cl.⁶ .............................................. A61B 5/00
[52] U.S. Cl. .................................. 128/635; 128/642; 128/662.06; 128/698; 128/736; 607/902
[58] Field of Search ............... 128/634, 635, 642, 670, 128/698, 736, 662.06; 607/902

[56] References Cited

U.S. PATENT DOCUMENTS

| 3,326,207 | 6/1967 | Egan. | |
|---|---|---|---|
| 4,873,986 | 10/1989 | Wallace | 128/670 |
| 5,184,619 | 2/1993 | Austin | 128/642 |
| 5,228,440 | 7/1993 | Chung et al. | |
| 5,247,932 | 9/1993 | Chung et al. | 128/642 |

FOREIGN PATENT DOCUMENTS

| 0097454 | 1/1984 | European Pat. Off. | |
|---|---|---|---|
| 645765 | 5/1937 | Germany. | |
| 2195897 | 4/1988 | United Kingdom | 128/642 |
| 2216804 | 10/1989 | United Kingdom | 128/634 |
| PCT/GB87/00713 | 4/1988 | WIPO. | |
| PCT/GB90/01708 | 6/1991 | WIPO. | |

OTHER PUBLICATIONS

"Prize Winning Probe Avoids Risk to Foetus", Hospital Doctor, vol. C10, No. 31, Aug. 1990.

Primary Examiner—Lee S. Cohen
Attorney, Agent, or Firm—Reinhart, Boerner, Van Deuren, Norris & Rieselbach

[57] ABSTRACT

An apparatus and method for noninvasively sensing parameters associated with the health of a fetus, the health of the placenta and the mother. The device includes a probe for inserting the sensor within the uterus of the mother, and the probe includes a flexible distal end portion having an independent inclination to assume an outward spiral curvature relative to the fetus. The probe has a transversely concave shaped channel to receive sensor cabling and control wires. The sensors can measure heart rate, oxygen saturation, temperature, chemical parameters, electroencephalogram activity and other useful parameters. The probe may also be used to infuse or remove fluid in the uterus.

28 Claims, 2 Drawing Sheets

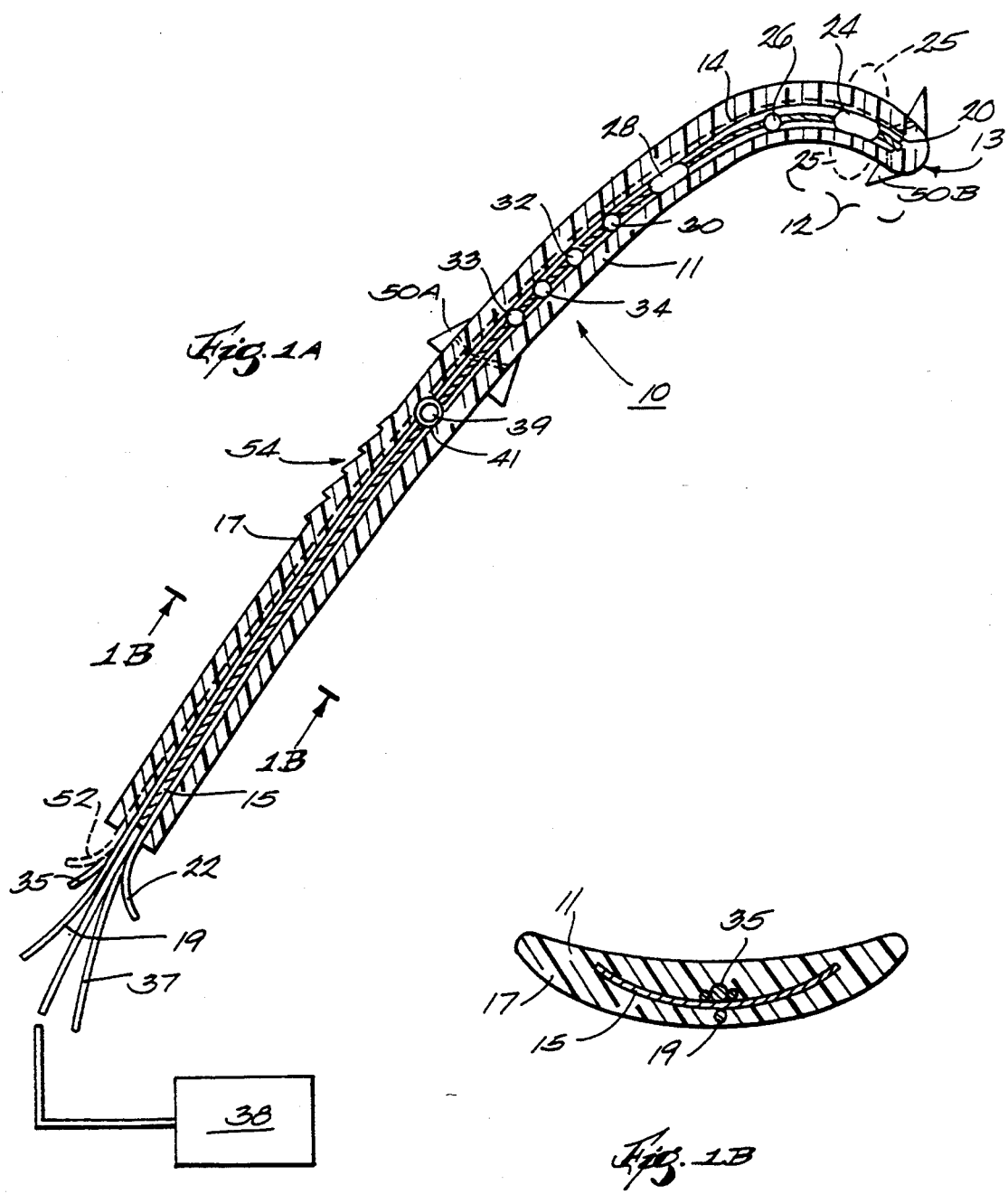

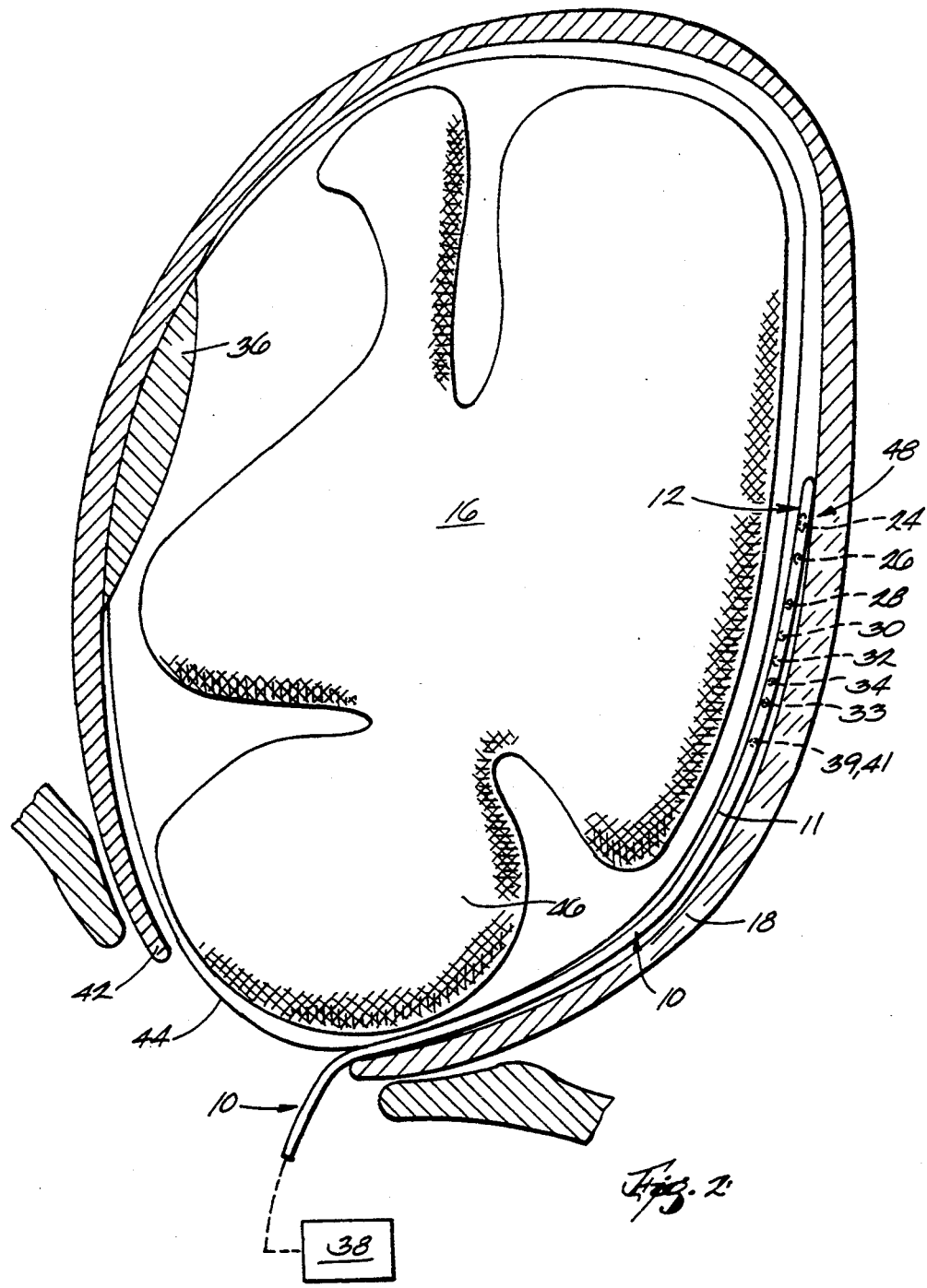

FETAL SENSOR DEVICE

The present invention is concerned generally with a sensor device and method for measuring vital signs of a human fetus and its mother. More particularly, the invention is concerned with a fetal sensor device positionable within the uterus of the mother, with amniotic membranes intact or ruptured, using a probe with a flexible, distal end. The flexible, distal end has an independent inclination to assume an outward spiral curvature relative to the fetus, or can wrap around the baby when not in spiral form, allowing easy positioning at a variety of useful fetal locations.

Conventional apparatus, such as an invasive cardiotocogram (CTG), uses invasive probes for monitoring fetal heart rate. Such an internal CTG probe penetrates the fetal tissues. These invasive probes can lead to infection of the fetus and/or the mother; and the probes are easily dislodged, and currently can measure only R-R intervals of the fetal ECG. The CTG method also attempts to predict oxygen saturation of the fetus by indirect examination of fetal heart rate. In addition, prior art devices are frequently able to perform only a few specific, limited measurements, not being able to monitor fetal wellness in addition to the mother's vital signs.

Furthermore, conventional fetal sensor devices are difficult to insert into the uterus and require substantial training to safely insert and maintain in an effective data-collection location. Moreover, the conventional methodology of placement in the vicinity of the fetal cranium can measure only poor blood perfusion in the fetal scalp and face, because: (1) The cervix can cause a tourniquet-like effect on the fetal scalp and face, (2) a hematoma formation under the fetal scalp during labor can interfere with oxygen saturation and cause lowered readings and, (3) placement near the cranium can also cause decreased blood flow in the fetal presenting part during labor contractions. In addition, conventional devices do not make reliable contact with the ferns thereby resulting in a very low percentage of useful data. Such conventional structures also readily allow expulsion of the sensor during labor.

It is, therefore, an object of the invention to provide an improved apparatus and method for monitoring fetal vitality.

It is another object of the invention to provide a novel fetal sensor apparatus and method for providing highly reliable data characteristic of fetal health, as well as the mother's health.

It is yet a further object of the invention to provide an improved fetal sensor device and method of use allowing stable positioning within the mother without being intrusive to the ferns.

It is an additional object of the invention to provide a novel fetal sensor device and method of use allowing sensing of a plurality of useful biological parameters of the ferns and the mother.

It is still another object of the invention to provide an improved fetal pressure sensor utilizing an inflatable balloon which can also selectively be used for engagement of the fetal sensor with the ferns and the placenta, and further for measurement of the force of contractions.

It is yet another object of the invention to provide a novel fetal sensor device and method of use allowing placement in a wide variety of biological sites to provide reliable wellness data for the ferns and mother.

It is still a further object of the invention to provide an improved fetal sensor device and method of use allowing easy atraumatic advancement of the device between the cervix and fetus and allowing placement within the uterus for reliable data collection while simultaneously minimizing insult to the ferns.

It is also an object of the invention to provide a novel fetal sensor device allowing incorporation of sensor leads without effecting uterine insertion, positioning and removal, and further providing accumulation of a multiplicity of data parameters for wellness evaluation.

These and other objects of the invention will become apparent from the detailed description hereinafter and the drawings hereinbelow described.

BRIEF DESCRIPTION OF THE DRAWINGS

FIG. 1A illustrates a fetal sensor device constructed in accordance with the invention and FIG. 1B is a cross section taken along 1B—1B in FIG. 1A; and FIG. 2 illustrates a cross-sectional view of a fetus in the mother's uterus with the fetal sensor disposed therein for wellness measurements.

DETAILED DESCRIPTION OF PREFERRED EMBODIMENTS

A fetal sensor device constructed in accordance with the invention is 'shown generally at 10 in the figures and, more particularly in FIG. 1. The fetal sensor device 10 (hereinafter "device 10") includes a housing 11 and a flexible distal end portion 12 with a soft molded tip 13. Preferably the distal end portion 12 is integrally coupled to the remainder of the device 10. The flexible distal end portion 12 and the soft molded tip 13 help minimize the possibility of membrane rupture. As shown best in FIG. 1B, the device 10 includes a flexible strip 15 (such as spring steed coated with a smooth surfaced coveting 17 (such as a silicone rubber or Teflon).

The flexible distal end portion 12 enables positioning of the device 10 at any one of a variety of positions within uterus 18 of the mother as shown in FIG. 2 The distal end portion 12 preferably further includes an independent inclination to assume a spiral curvature outward relative to fetus 16 (curving away therefrom) to assist in easy insertion, positioning and removal of the device 10 from the uterus 18. In one preferred embodiment in order to control the outward spiral curvature, the device 10 can also include a displaceable wire-like element 19 (in phantom in FIG. 1A). The wire-like element 19 is fixed at distal point 20 and movable by the clinician at proximal end 22 to assist in establishing the desired curvature for insertion, positioning and removal from the uterus 18. In other forms of the invention, the flexible distal end portion 12 can assume a flat position rather than a spiral curvature in order to follow closely the contour of the fetus 16 or the interior of uterus 18 of the mother.

The device 10 can include preferably one or more of a variety of sensors, such as a pressure sensor 24, an ECG sensor 26, an EEG sensor 28, a temperature sensor 30, an oxygen sensor 32, an ultrasound transducer/sensor 33, a laser diode 39 emitting IR signals with an associated sensor 41 and a chemical sensor 34. The device 10 preferably includes a dished shape or transversely concave geometry (see FIG. 1B) which allows positioning of sensor cable 35 and the sensors within the protective concave valley to minimize mechanical interaction with the uterus 18 and the fetus 16. This diskshaped geometry also allows easy, atraumatic advancement between cervix 42 and the fetus 16. In the most preferred embodiment the device 10 has a width of about 1-3 centimeters and 25-33 centimeters in length. The 1-3 centimeter width dimension helps prevent twisting of the device 10 when being inserted into the uterus 18 or being positioned for use in sensing fetal parameters. The 25-35 centimeter length enables positioning of the sensor means along a substantial path length of interest, as well as being able to easily reach a normally remote location within the uterus 18. In addition, placement of the device 10 well within the uterus 18 avoids a number of problems associated with conventional sensors disposed near the cervix 42 or fetal cranium 46, such as: (a) creation of a tonsure effect (a tourniquet effect caused by the cervix 42), (b) caput which is a hematoma formation under the fetal scalp generated during labor, (c) poor blood perfusion caused by the fetal cranium 46 engaging the cervix 42, (d) maternal contractions causing decreased flow to the presenting part, (e) inconsistent sensor contact arising from poor mechanical contact, fetal hair interference or motion artifact in the pelvic area, and (f) inadvertent extrusion of the device 10 due to maternal labor or cable traction.

The pressure sensor 24 can include a balloon type device 25 which can be inflated (see in phantom the balloon device 25 in FIG. 1A) to variable pressures and used with conventional feed back electronics in control unit 38 to maintain a substantially constant pressure of engagement of the device 10 with at least one of the fetus 16 and the uterus 18 of the mother. The balloon type device 25 of the pressure sensor 24 can also be used in conjunction with conventional electronics in control unit 38 to directly sense the pressure within the uterus 18. Such pressure readings can provide an indication of the progress of labor. Similarly the other sensor devices provide important information as to the state of wellness without intrusive probing of the fetus 16. As can be seen by reference to FIG. 2, the device 10 can be positioned readily at any time, including prior to rupture of maternal membranes, with minimum risk to the fetus 16 and the mother (not shown). Since monitoring can be performed with intact maternal membranes, it can be useful to know the location of placenta 36 in order to avoid disturbing its fixation to the uterus 18. This can be accomplished by such conventional methods as an ultrasound scan of the mother's abdomen. The device 10 itself can also be fitted with an ultrasound device (e.g., the transducer/sensor 33) to assess the fetal heart or other fetal structures. Also, the device 10 can be utilized to allow inflation or deflation of the uterus 18 with fluids passed through channel 37 (see, FIG. 1A) to enable selected careful changes of the fetal position.

Using the knowledge of the placental location, the device 10 can be manually inserted within the uterus 18 to a position desired. This can be done, for example, by using one hand to guide the device 10 and the other to push the device 10 between the cervix 42 and that portion of amniotic sac 44 covering the fetal cranium 46. Once a desired insertion path is established, the device 10 is readily advanced while the clinician observes a display (part of the control unit 38) to determine an acceptable plethysmographic signal. The previously described distal end portion 12 assists in establishing a stable position for the device 10, and the position may require adjustment following labor contractions or patient position changes. Experimentation in clinical settings have determined a wide variety of stable positions can be achieved for the device 10, and a preferable position is posterior to the ferns 16 known as ausculatory position 48 (shown generally in FIG. 2). In such a location the previously described geometry of the device 10 prevents twisting of the distal end portion 12 which would result in the sensor facing the uterine wall rather than the ferns 16. Exact placement of the device 10 can also be determined using ultrasound techniques (such as operating an external ultrasound system or the transducer/sensor 33 ).

In a preferred embodiment the device 10 uses the various sensors described hereinbefore to measure fetal heart rate (the ECG sensor 26), oxygen saturation in the fetal blood (the oxygen sensor 32), and differences in fetal versus uterine temperature (the temperature sensor 30) to allow a three-pronged decision tree analysis to assess fetal wellness. If there is uterine-placental-fetal insufficiency, there is usually a rapid rise in fetal temperature since fetal heat loss is facilitated by heat exchange by the well-perfused placenta 36. Performance of oximetry studies can differentiate between clinically insignificant marginal heart rate values and significant fetal distress. It is also useful to accumulate ECG data to ascertain the need to deliver a child when a condition of fetal distress occurs. Furthermore, the device 10 allows more accurate characterization of fetal and maternal parameters, and this avoids false indications of distress which can lead to unnecessary clinical procedures.

In another form of the invention, a light source, such as the laser diode 39 with accompanying light sensor 41 (see FIG. 1A), can be used to determine the proximity of the device 10 to the tissue of the fetus 16. Using a photon wavelength which is more prone to reflectance from the fetal tissue and also to significant absorption through the tissue, there is an intensity component characteristic of the proximity of engagement of the laser diode 39 and light sensor 41 to the fetal tissue. When the diode 39 is in contact with the fetal tissue, the signal detected by the light sensor 41 will be quite small. However, as the diode 39 (and the coupled device 10) pull away from the fetal tissue, the light intensity detected by the light sensor 41 will increase substantially. Thus, for purposes of optimizing data collection or insuring reliable monitoring, it would be useful to know the spacing of the device 10 from the fetal tissue. For example, the best quality signal from the oxygen sensor 32 occurs when it is in direct contact with the fetus 16 and has a small amount of positive pressure applied to the monitoring site. Therefore, the measure of oxygen saturation can be optimized by monitoring the positional status or proximity to the fetal tissue of the sensor 32 using the diode 39 and the accompanying light sensor 41.

In yet another form of the invention, the diode 39 and accompanying light sensor 41, or the like, can be used to identify and compensate or cancel motion artifacts generated at the monitoring site. This compensating function can be achieved in a number of ways. For example, the diode 39 can provide monitoring signals indicative of excessive variations in signal level. These monitoring signals can be used to stop calculations of oxygen saturation during periods of motion artifact. In another approach, the oxygen saturation level can be calculated redundantly for several wavelength pairs and averaged to reduce motion artifact errors introduced in the data. Another method can involve isolation of two data channels which are least affected by the motion and then carry out calculation of the oxygen saturation value using these two data channels, each being characteristic of two different light wavelengths. A further method can be selection of a wavelength which is characteristic of pure motion artifact information. This particular data can then be scaled and subtracted from two other channels being used for oxygen saturation calculation in order to minimize the motion artifact signal superimposed on the oxygen saturation signal.

In another preferred embodiment, the chemical sensor 34 can be an ionic sensor for evaluating electrolyte compositions of the amniotic fluid. Such analyses can provide important indications of the status of development of the fetus and signs of fetal distress.

In another form of the invention, the device 10 can include means for resisting expulsion from the uterus 18. As shown in FIG. 1A, such means can include, for example, an arrow tip structures 50A and 50B disposed on the housing 11. The arrow tip structures 50A and/or 50B can be coupled to a control wire 52 enabling selective opening and closing (that is, positioned flush with the housing 11) to activate/deactivate the anchoring effect. Other such means for resisting expulsion of the device 10 can be a fish scale layer 54 disposed on the housing 11.

The following nonlimiting example sets forth operating results for a preferred embodiment of the invention.

EXAMPLE

A fetal sensor was prepared having the structure described in the specification (and shown in FIG. 2 in particular) using the curved distal end portion of the sensor device to position the distal end portion at the ausculatory site of a fetus. Data were accumulated from thirty five different patients, and the results are summarized in the Table below.

Illustrated in the Table are data from women in active labor with intact membranes. The age in years of the patient is shown, and date and time are also shown. Also shown is the percentage of acceptable data measured when fetal oximetry data were obtained, which includes a plesthysmograph wave form. Monitoring was performed beginning near the onset of labor and carried out over the time period indicated. The percentage of acceptable data is a measure of the useful data taken over the entire labor period. Mean fetal heart rate is calculated and is shown to correspond well with CTG and fetal stethascoptical examination with essentially no clinical differences.

While preferred embodiments of the invention have been shown and described, it will be clear to those skilled in the art that various changes and modifications can be made without departing from the invention in its broader aspects as set forth in the claims provided hereinafter.

TABLE I

| | | | | | | | | | | | |
|---|---|---|---|---|---|---|---|---|---|---|---|
| | | | | | FETAL OXIMETRY DATA | | | | | | |
| Pt. # | Date | Time of Day (Labor) | Age | Gravida (no. of times pregnant) | Para (no of live births) | Time Monitored (min.) | % Data OK | Oxy. Sat % (Mean) | Mean Fetal Heart Rate | CTG/FHR | Stethoscopic FHR |
| 1 | 3-Nov | 1430 | 26 | 6 | 5 | 25 | 99 | 63.4 | 130 | | 125 |
| 2 | 10-Nov | 946 | 22 | 2 | 1 | 24 | 99.2 | 63.5 | 136.25 | | 130 |
| 3 | 30-Oct | 1034 | 18 | 1 | 0 | 59 | 88 | 69.5 | 145 | | 140 |
| 4 | 3-Nov | 1004 | 26 | 1 | 0 | 45 | 99.5 | 63.16 | 161.66 | | 160 |
| 5 | 29-Oct | 1339 | 26 | 1 | 0 | 26 | 87.3 | 60.66 | 138.33 | | 140 |
| 6 | 1-Nov | 1324 | 18 | 1 | 0 | 59 | 95 | 61.34 | 139.64 | | 140 |
| 7 | 8-May | 1214 | 23 | 1 | 0 | 66 | 100 | 81.43 | 170 | | 160 |
| 8 | 8-May | 1029 | 21 | 4 | 3 | 7 | 100 | 67 | 157.5 | 150 | |
| 9 | 6-May | 836 | 26 | 4 | 3 | 10 | 99 | 63.7 | 143.42 | 140 | |
| 10 | 6-May | 908 | 23 | 3 | 2 | 11 | 96 | 70.8 | 155.6 | 155 | |
| 11 | 6-May | 742 | 21 | 1 | 0 | 10 | 100 | 62.1 | 137.2 | 140 | |
| 12 | 30-Apr | 2224 | | | | 18 | 96 | 51.62 | 141.4 | 0 | 142 |
| 13 | 1-May | 1802 | 21 | 1 | 0 | 53 | 92 | 65.24 | 133.6 | 133.7 | |
| 14 | 3-May | 2052 | 24 | 1 | 0 | 34 | 88 | 69.81 | 152.2 | 151 | |
| 15 | 3-May | 932 | 17 | 1 | 0 | 34 | 84 | 67.1 | 160.6 | 142.3 | |
| 16 | 1-Feb | 1114 | | | | 214 | 98 | 67.25 | 150.6 | 0 | 100 |
| 17 | 30-Jan | 1307 | 18 | 1 | 0 | 46 | 86.5 | 67.65 | 150.1 | 0 | 125 |
| 18 | 30-Jan | 1521 | 39 | 3 | 2 | 23 | 98.4 | 50.1 | 123.55 | 0 | 120 |
| 19 | 29-Jan | 1133 | 18 | 1 | 0 | 30 | 80.3 | 61.3 | 139.92 | 0 | 130 |
| 20 | 1-May | 1643 | 31 | 4 | 2 | 56 | 70 | 42.5 | 147.74 | 0 | 150 |
| 21 | 1-Feb | 1231 | 30 | 4 | 1 | 135 | 90.3 | 58.19 | 146.8 | 0 | 140 |
| 22 | 4-May | 2116 | 28 | 3 | 2 | 32 | 96 | 71.57 | 154.77 | 142 | 160 |
| 23 | 2-Feb | 2135 | | | | 13 | 49 | 62.24 | 146.2 | 0 | 140 |
| 24 | 2-Feb | 1840 | 23 | 1 | 0 | 48 | 94 | 61.86 | 140.83 | 0 | 130 |
| 25 | 2-May | 1007 | 22 | 1 | 0 | 68 | 96 | 53.51 | 123.1 | 134.7 | |
| 26 | 2-May | 1248 | 37 | 8 | 7 | 158 | 98 | 57.16 | 129.2 | 137.01 | |
| 27 | 30-Jan | 1307 | 24 | 2 | 1 | 31 | 94 | 65 | 150.1 | 0 | 140 |
| 28 | 29-Oct | 1137 | 26 | 1 | 0 | 81 | 92 | 62 | 132 | 0 | 130 |
| 29 | 30-Oct | 1117 | | | | 28 | 80 | 75 | 140 | 0 | 140 |
| 30 | 1-Nov | 1621 | | | | 17 | 92 | 65 | 142 | 0 | 136 |
| 31 | 1-Nov | 1849 | | | | 49 | 99 | 63 | 148 | 0 | 140 |
| 32 | 4-Nov | 1417 | 22 | 2 | 1 | 8 | 75 | 70 | 150 | 0 | 146 |
| 33 | 4-Nov | 935 | 22 | 2 | 1 | 38 | 95 | 60 | 135 | 0 | 140 |
| 34 | 7-May | 752 | 26 | 5 | 2 | 33 | 96 | 76 | 144 | 0 | 140 |
| 35 | 7-May | 929 | 28 | 3 | 2 | 10 | 100 | 59 | 142 | 0 | 140 |
| | | | | | | 1599 | 3201.5 | 2228.69 | 6027.31 | 1425.71 | |
| | | | | | | 45.68571429 | 91.47143 | 63.67686 | 143.637 | 142.571 | |
| | | | | | | 10.60660172 | 0.707107 | 3.11127 | 8.48528 | 9.1923816 | |

What is claimed is:

1. A fetal sensor device for measuring biological parameters associated with a fetus, a placenta and a mother of the fetus, comprising:

means for noninvasively sensing parameters associated with at least one of the health of the fetus, the health of the placenta and of the mother bearing the fetus; and probe means for inserting said means for sensing within a uterus of the mother, said probe means having a housing and including a flexible distal end portion integrally part of said probe means housing for positioning said means for sensing at a selected location in the mother and said distal end portion further having an independent inclination to assume an outward spiral curvature relative to the fetus.

2. The fetal sensor device as defined in claim 1 further including means for controlling curvature of said distal end portion of said probe means.

3. The fetal sensor device as defined in claim 1 wherein said distal end portion of said probe means includes a terminus and wherein said sensing means is disposed before said terminus of said distal end portion of said probe means.

4. The fetal sensor device as defined in claim 1 wherein said sensor means includes at least one of an ECG sensor, an EEG sensor, a temperature sensor, a pressure sensor, an oximetry sensor, an electrochemical sensor, a chemical sensor, and an ultrasound transducer array.

5. The fetal sensor device as defined in claim 4 wherein said chemical sensor comprises an ionic sensor for evaluating electrolyte compositions of amniotic fluid.

6. The fetal sensor device as defined in claim 1 wherein said probe means includes a longitudinal channel with a transversely concave surface for containing said sensor means.

7. The fetal sensor device as defined in claim 6 further including a sensor coupling disposed in said longitudinal channel and coupled to said means for sensing.

8. The fetal sensor device as defined in claim 1 further including an inflatable balloon device coupled to said probe means for directly sensing pressure.

9. The fetal sensor device as defined in claim 8 further including means for inflating said balloon device with dynamically variable pressures.

10. A method of sensing biologically useful parameters associated with a human fetus, comprising the steps of:

providing a probe having a housing including a flexible distal end portion and means for sensing the biologically useful parameters;

inserting said probe within the uterus of the fetus' mother to place said means for sensing at a selected location near the fetus;

positioning said means for sensing by using said flexible distal end portion having an independent inclination to assume an outward spiral curvature relative to the fetus; and using said means for sensing to measure the biologically useful parameters.

11. The method as defined in claim 10 wherein the positioning step comprises locating said means for sensing near an auscultatory site of the fetus.

12. (Amended) The method as defined in claim 10 further including the step of providing an inflatable balloon coupled to said probe, said balloon enabling performing the additional step of measuring pressure near the fetus.

13. The method as defined in claim 10 further including the step of controlling the outward spiral curvature of said flexible distal end portion to enable firm positioning of said probe relative to the fetus.

14. The method as defined in claim 10 wherein said biologically useful parameters comprise at least one of oxygen content in the fetus' blood, temperature, ECG data and chemical parameters associated with the fetus.

15. The method as defined in claim 10 further comprising the step of providing said probe with a transversely concave surface enabling easy insertion of said probe into the uterus of the mother.

16. The method as defined in claim 10 further comprising the step of providing said probe with means for resisting expulsion from the uterus.

17. The method as defined in claim 16 further comprising the step of providing said means for resisting expulsion with an arrow tip structure disposed on said probe.

18. The method as defined in claim 16 further comprising the step of providing said means for resisting expulsion with a fish scale layer disposed on said probe.

19. The method as defined in claim 10 further including the step of responding to said biologically useful parameters to infuse or remove fluids from the uterus.

20. A method of sensing biologically useful parameters associated with a human fetus, comprising the steps of:

providing a probe having a housing including a flexible distal end portion and means for sensing the biologically useful parameters;

inserting said probe into a natural body cavity of the mother of the human fetus;

positioning said means for sensing by using said flexible distal end portion having an independent inclination to assume an outward spiral curvature within the natural body cavity; and activating said means for sensing to measure the biologically useful parameter.

21. The method as defined in claim 20 further comprising the step of providing said probe with a longitudinal channel shaped device having a transversely concave surface.

22. The method as defined in claim 21 further comprising the step of dimensioning said device about 1–3 centimeters wide and about 20–35 centimeters long.

23. The method as defined in claim 22 further comprising the step of providing said device with a silicone based plastic covering over a spring steel strip.

24. The method as defined in claim 20 wherein the positioning step comprises locating said distal end portion at an auscultatory site of the human fetus.

25. The method as defined in claim 20 further comprising the step of providing said distal end portion with an arrowed portion for anchoring said probe.

26. The method as defined in claim 20 further comprising the step of providing said means for sensing with a sensor for determining motion artifacts.

27. The method as defined in claim 20 further comprising the step of providing said means for sensing with means for determining proximity of said housing to the human fetus.

28. The method as defined in claim 20 further comprising the step of providing said means for sensing with a light source and sensor for detecting the presence of artifacts arising from motion and thereby enabling correction of data characteristic of the biologically useful parameters.

* * * * *

UNITED STATES PATENT AND TRADEMARK OFFICE
CERTIFICATE OF CORRECTION

PATENT NO. : 5,425,362

DATED : June 20, 1995

INVENTOR(S) : Daniel Siker, Michael T. Larsen, NC Joseph Lai

It is certified that error appears in the above-identified patent and that said Letters Patent is hereby corrected as shown below:

```
    Col. 1, Line 40, cancel "ferns" and insert --fetus--;
    Col. 1, Line 54, cancel "ferns" and insert --fetus--;
    Col. 1, Line 58, cancel "ferns" and insert --fetus--;
    Col. 1, Line 62, cancel "ferns" and insert --fetus--;
    Col. 1, Line 68, cancel "ferns" and insert --fetus--;
    Col. 2, Line 27, cancel "'" before shown;
    Col. 2, Line 36, cancel "steed" and insert --steel)--;
    Col. 2, Line 37, cancel "coveting" and insert --covering--;

Col. 4, Line 3, cancel "ferns" and insert --fetus--;
    Col. 4, Line 8, cancel "ferns" and insert --fetus--;
Col. 5-6, In Table I, Row 19, Col. Mean Fetal Heart Rate, cancel
    "139.92" and insert --138.92--;
    In Table I, Row 32, Col. Age, cancel "22".
```

Signed and Sealed this

Fourteenth Day of November, 1995

*Attest:*

BRUCE LEHMAN

*Attesting Officer*  Commissioner of Patents and Trademarks